(12) United States Patent
Stürmer

(10) Patent No.: US 7,435,835 B2
(45) Date of Patent: Oct. 14, 2008

(54) METHOD FOR PRODUCING ENANTIOMER-PURE AMINOALCOHOLS

(75) Inventor: Rainer Stürmer, Rödersheim-Gronau (DE)

(73) Assignee: BASF AG, Ludwigshafen (DE)

( * ) Notice: Subject to any disclaimer, the term of this patent is extended or adjusted under 35 U.S.C. 154(b) by 139 days.

(21) Appl. No.: 10/587,440

(22) PCT Filed: Jan. 18, 2005

(86) PCT No.: PCT/EP2005/000420

§ 371 (c)(1),
(2), (4) Date: Jul. 26, 2006

(87) PCT Pub. No.: WO2005/073215

PCT Pub. Date: Aug. 11, 2005

(65) Prior Publication Data

US 2007/0128704 A1      Jun. 7, 2007

(30) Foreign Application Priority Data

Jan. 29, 2004   (DE) ................. 10 2004 004 719

(51) Int. Cl.
*C07D 333/18* (2006.01)
*C07D 333/24* (2006.01)

(52) U.S. Cl. ............................ 549/78; 549/79
(58) Field of Classification Search ............. 549/78, 549/79
See application file for complete search history.

(56) References Cited

U.S. PATENT DOCUMENTS

| 5,312,950 A | * | 5/1994 | Boaz ........................ 558/51 |
| 5,362,886 A | | 11/1994 | Berglund |
| 5,914,263 A | * | 6/1999 | Buizer et al. ............... 435/280 |
| 2005/0245749 A1 | | 11/2005 | Stürmer |

FOREIGN PATENT DOCUMENTS

| EP | 0 273 658 | 7/1988 |
| EP | 0 457 559 | 11/1991 |
| EP | 1 300 405 | 4/2003 |
| JP | 02142495 | * 5/1990 |
| WO | WO-2004/013123 | 2/2004 |

OTHER PUBLICATIONS

Liu et al. Chirality 2000, 12, 26-29.*
Gutman et al. Tetrahedron: Asymmetry (1993), 4(5), 839-44.*
Nishio et al. STN Accession No: 1990:550895 Abstract of JP 02142495.*
Beilstein Institut zur Forderung der Wissenschaften, XP002333975 (2002) (2 pages total).
Liu, H. et al., "Chemo-Enzymatic Synthesis of the Antidepressant Duloxetine and Its Enantiomer", Chirality 12 (2000), pp. 26-29.
Deeter, J. et al., "Asymmetric Synthesis and Absolute Stereochemistry of LY248686", Tetrahedron Letters 31(49) (1990), pp, 7101-7104.
Wheeler, W. J. et al., "An Asymmetric Synthesis of Duloxetine Hydrochloride, a Mixed Uptake Inhibitor of Serotonin and Norepinephrine, and Its C-14 Labeled Isotopomers", Journal of Labelled Compounds and Radiopharmaceuticals 36 (1995), pp. 213-223.
Kamal, A. et al., "Chemoenzymatic Synthesis of Duloxetine and Its Enantiomer: Lipase-catalyzed Resolution of 3-hydroxy-3-(2-thienyl) Propanenitrile", Tetrahedron Letters 44 (2003), pp. 4783-4787.
Akita, H. et al., "Lipase Catalyzed Enantioselective Hydrolysis of 2-Methyl 3-Acetoxy Esters", Tetrahedron Letters 27 (43) (1986), pp. 5241-5244.
Singh, S. et al., "Chemoenzymatic Synthesis of Optically Active Heterocyclic Homoallylic and Homopropargylic Alcohols", Tetrahedron: Asymmetry 13 (2002), pp. 2679-2687.

* cited by examiner

*Primary Examiner*—D. Margaret Seaman
*Assistant Examiner*—Nizal S Chandrakumar
(74) *Attorney, Agent, or Firm*—Connolly Bove Lodge & Hutz LLP

(57) ABSTRACT

The invention relates to a process for preparing enantiomerically pure alcohol of the formula 1, which comprises
(i) reducing the ketone of the formula 3 to the racemic alcohol of the formula 4,
(ii) enantioselectively acylating the racemic alcohol of the formula 4 with succinic anhydride in the presence of a lipase to give the succinic semiester of the formula 7,
(iii) separating off the succinic semiester of the formula 7 from the unreacted enantiomer of the formula 4,
(iv) reacting the enantiomerically pure alcohol of the formula 4 with methylamine to give the enantiomerically pure alcohol of the formula 1.

17 Claims, 1 Drawing Sheet

METHOD FOR PRODUCING ENANTIOMER-PURE AMINOALCOHOLS

RELATED APPLICATIONS

Figure 1:
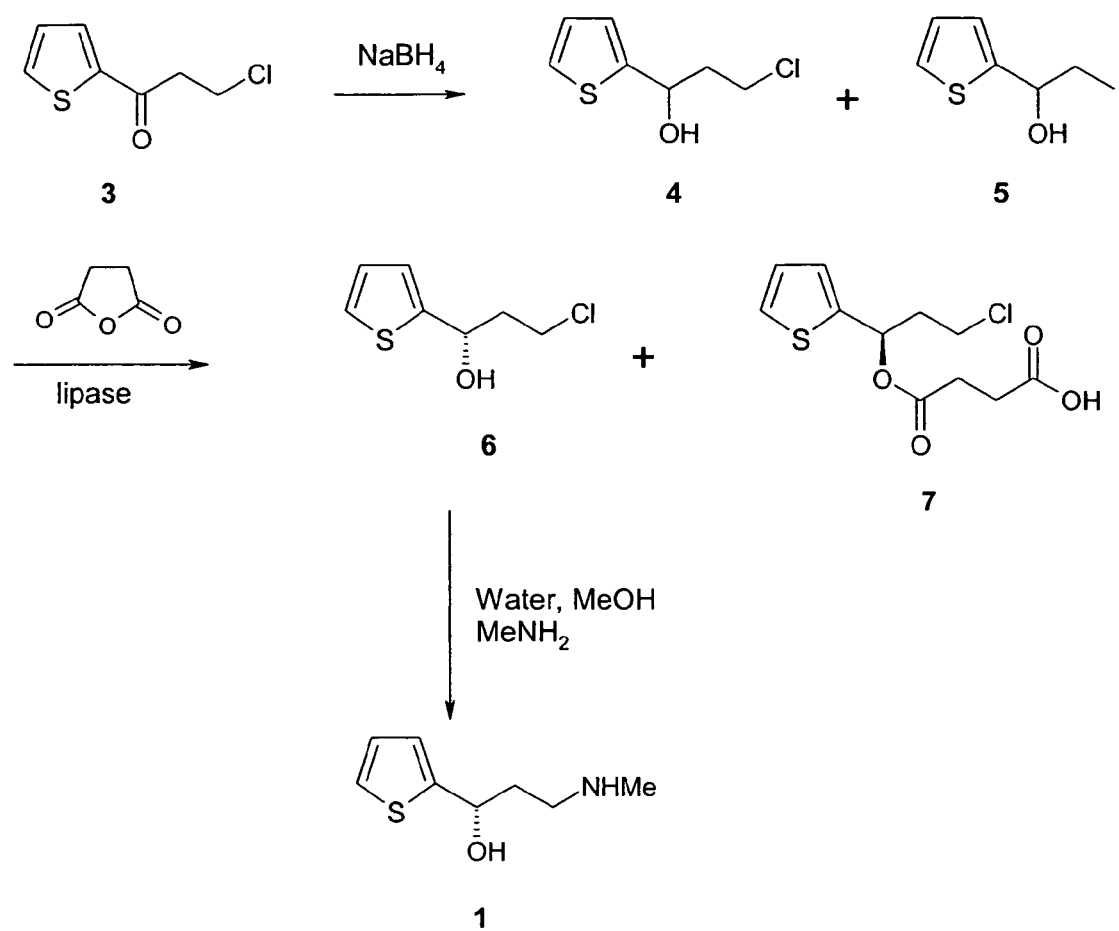

This application is a national stage application (under 35 U.S.C. 371) of PCT/EP2005/000420 filed Jan. 18, 2005, which claims benefit to German application 10 2004 004 719.7 filed Jan. 29, 2004.

The aminoalcohol 1 (FIG. 1) [(1S)-3-methylamino-1-(2-thienyl)propan-1-ol] is a sought-after intermediate when producing the pharmaceutical Duloxetine® ((+)-(S)—N-methyl-3-(1-naphthyloxy)-3-(2-thienyl)propylamine oxalate). The method which has previously been used for preparing this intermediate is elaborate and requires reagents which are expensive and labile. In addition, a technically elaborate chromatography is required for preparing a pure compound, see, for example, EP 273658 A1; Liu et. al., Chirality 2000, 12 (1), 26-29; Wheeler et al., J. Labelled Comp. Radiopharm. 1995, 36(3), 213-23; U.S. Pat. No. 5,362,886, EP 457559, Deeter et al., Tet. Lett. 1990, 31(49), 7101-4.

It was therefore the object of the present invention to provide processes for producing Duloxetine®, or its precursors, which are simpler and more economical.

The present invention describes a novel, economical route to the isomerically pure compound. A method for separating off an unwanted by-product in a simple manner, without chromatography, is also described.

The synthesis according to the invention, which starts from the ketone 3 [3-chloro-1-(2-thienyl)-1-propanone] is shown in FIG. 1:

(i) The invention relates to a process for preparing enantiomerically pure alcohol of the formula 1, which comprises
(ii) reducing the ketone of the formula 3 to the racemic alcohol of the formula 4,
(iii) enantioselectively acylating the racemic alcohol of the formula 4 with succinic anhydride in the presence of a lipase to give the succinic semiester of the formula 7,
(iv) separating off the succinic semiester of the formula 7 from the unreacted enantiomer of the formula 4,
(v) reacting the enantiomerically pure alcohol of the formula 4 with methylamine to give the enantiomerically pure alcohol of the formula 1.

The alcohol 4 is generated, in racemic form, by reducing the corresponding ketone 3 [3-chloro-1-(2-thienyl)-1-propanone], as the starting compound, with, for example, borohydride, preferably $NaBH_4$ (step (i)). However, the alcohol 5 [1-(2-thienyl)propan-1-ol], which is formed by hydrogenation of the chlorine function, also appears at a low percentage as a by-product during this reduction. The by-product (alcohol 5) amounts to between 1 and 15% of the quantity of the ketone 3 employed. Separating this alcohol 5 from the product 4 at this step is difficult and requires elaborate chromatography.

Advantageously, this impurity is separated off in the last step (step (iv)) in connection with the reaction with methylamine since 5 does not react with methylamine and does not crystallize, either.

In the next step (step (ii)), the racemic alcohol 4 is enantioselectively acylated with succinic anhydride in the presence of a lipase to give the succinic semiester 7, i.e. one enantiomer reacts with the succinic anhydride while the other enantiomer remains unaltered. The stereospecificity of the lipase is responsible for the selectivity of the acylation in this reaction.

As a rule, the R enantiomer of the alcohol 4 is acylated to give the succinic semiester 7 under the described conditions whereas the S enantiomer of 4 (=6) remains unaltered.

A large number of lipases which are used in organic synthesis are suitable for the process according to the invention (K. Faber, "Biotransformations in Organic Chemistry", Springer Verlag, Berlin, 2nd edition, 1995).

Lipases of the homology families I.1 and I.2, as classified in accordance with Arpigny and Jäger (Biochem. J. 1999, 343, 177-183, Table 1), are particularly suitable. Of these, the lipases which can be isolated from *Pseudomonas* strains, for example from *Pseudomonas aeruginosa*, *Pseudomonas fragi*, *Pseudomonas wisconsinensis*, *Pseudomonas fluorescens*, *Pseudomonas vulgaris*, *Pseudomonas luteola* and *Pseudomonas* spec. DSM8246, from *Burkholderia* strains, for example *Burkholderia cepacia*, *Burkholderia glumae* and *Burkholderia plantarii*, and also from *Acinetobacter calcoaceticus*, *Chromobacterium viscosum* and *Vibrio cholerae*, are particularly suitable.

In addition, lipases which have been obtained by using genetic engineering to alter, adapt or optimize the abovementioned lipases are also suitable for the process according to the invention.

The lipases can be used in the form of whole cells, as a cell-free extract or in the form of purified proteins. Particular preference is given to using the lipases in the form of partially purified or highly purified protein solutions.

The lipases can also be immobilized on a support, using methods known to the skilled person, and then employed in the process according to the invention (e.g. Persson et al. Biotechnology Letters 2000, 22(19) 1571-1575). Using immobilized lipases is a preferred embodiment particularly when conducting the process continuously. For this purpose, the lipases can advantageously be used while being immobilized in a column or a tubular reactor.

The reaction (step (ii)) preferably takes place in an organic solvent, for example a hydrocarbon or an ester.

Solvents which are particularly suitable for the reaction in step (ii) are aliphatic hydrocarbons such as hexane, heptane and octane or mixtures thereof. Other solvents which are highly suitable are aromatic hydrocarbons, in particular benzene and toluene. The lower alkyl esters of carbonic acid, such as ethylene carbonate or propylene carbonate, are also highly suitable.

In a further reaction (step (iii)), the succinic semiester (7) is now separated from unreacted enantiomer (6). This is expediently effected by extracting the succinic semiester (7) or its salt, in particular its alkali metal salt, with an aqueous phase. A preferred embodiment is the aqueous extraction in the presence of sodium carbonate which is described in Example 2.

Depending on which enantiomer of the alcohol 4 is required, either the organic phase, which contains the enantiomer 6, or the aqueous phase, which contains the other enantiomer in the form of the succinic semiester 7, can now be worked up. Customary methods of hydrolysis can be used to cleave the succinic semiester 7 into succinic acid and the enantiomer of the alcohol.

In a further reaction (step (iv)), the desired enantiomerically pure alcohol is reacted with methylamine to give the enantiomerically pure aminoalcohol 1.

This usually takes place using methylamine in the presence of water and methanol, as described in Example 3. At this step, the by-product 5, a small quantity of which was formed in step (i) and which has thus far been entrained, is separated off since it does not react with methylamine and can readily be removed when 1 is subsequently purified, for example by means of recrystallization.

The aminoalcohol 1, which can be prepared in high enantiomeric purity using the process according to the invention, is a sought-after precursor for producing the initially mentioned pharmaceutical Duloxetine®.

EXAMPLE 1

Preparing 4 [3-chloro-1-(2-thienyl)propan-1-ol]

204 g (1.21 mol) of ketone 3 are initially introduced, at 0° C., in a mixture composed of 400 ml of toluene and 200 g of methanol. After 2 g of 30% NaOH have been added, 21.4 g of sodium borohydride are added in portions within the space of 2.5 h. After the reaction mixture has been stirred at 0° C. for 40 min, it is added to 500 ml of ice-cold 10% acetic acid. After the aqueous phase has been separated off, the organic phase is dried over sodium sulfate and freed from the solvent. 198 g of 4, which contains approx. 10% of 5, are obtained.

EXAMPLE 2

Preparing 6 [(1S)-3-chloro-1-(2-thienyl)propan-1-ol]

197 g (1.16 mol) of alcohol 4, containing 10% of alcohol 5 (i.e. the reaction product obtained from Example 1), are initially introduced in 1 liter of MTBE. 64.4 g (0.64 mol) of succinic anhydride and 10 g of *Burkholderia plantarii* lipase are then added. The mixture is stirred at RT for 20 h and freed from the enzyme by filtration. After 1.4 l of water have been added, the mixture is adjusted to pH=9 with sodium carbonate and the aqueous phase is separated off. The organic phase is dried over sodium sulfate and freed from the solvent. 96 g of 6, which contains approx. 10% of the corresponding antipode of 5, are obtained.

EXAMPLE 3

Preparing 1 [(1S)-3-methylamino-1-(2-thienyl)propan-1-ol]

20 g (0.093 mol) of alcohol 6, containing approx. 10% of the corresponding antipode of 5 (i.e. the reaction product from Example 2), are initially introduced, in 40 g of methanol, in a pressurized vessel, after which 74 g of a 40% solution of methylamine in water are added and the mixture is stirred, at 75° C. for 20 h, under intrinsic pressure. After the reaction has come to an end, 5 g of 30% NaOH are added and the mixture is stirred at 80° C. for 10 min. The solvent is removed and the residue is taken up in 100 ml of toluene. After the insoluble constituents have been filtered off, the residue is recrystallized from cyclohexane.

13.17 g of colorless crystals of 1 were obtained (angle of rotation: c=1 in MeOH, alpha[D]25° C.=−13.2°, corresponding to an optically pure product.

FIG. 1 describes the reaction scheme for preparing (1S)-3-methylamino-1-(2-thienyl)propan-1-ol from 3-chloro-1-(2-thienyl)-1-propanone.

I claim:
1. A process for preparing enantiomerically pure alcohol of the formula 1, which comprises

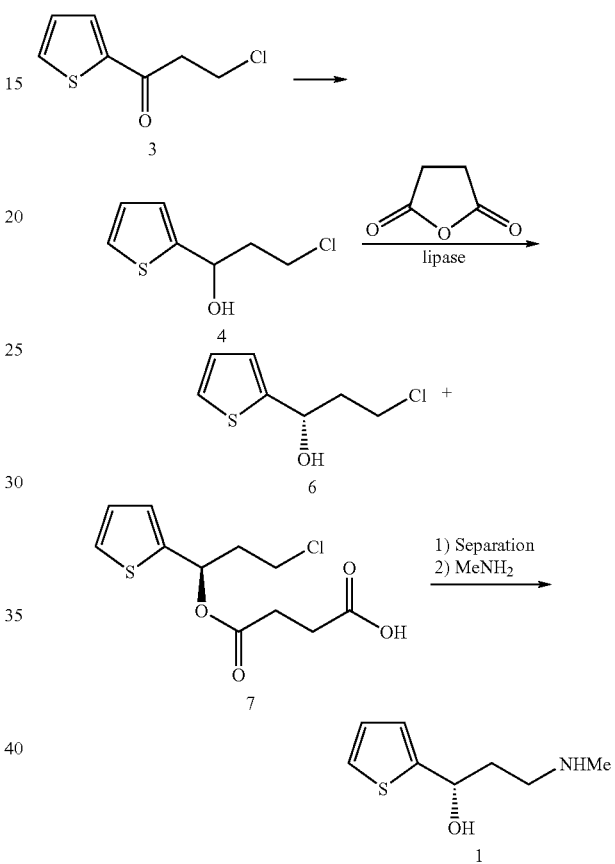

(i) reducing the ketone of the formula 3 to the racemic alcohol of the formula 4,
(ii) enantioselectively acylating the racemic alcohol of the formula 4 with succinic anhydride in the presence of a lipase to give the succinic semiester of the formula 7,
(iii) separating off the succinic semiester of the formula 7 from the unreacted enantiomer of the formula 4,
(iv) reacting the enantiomerically pure alcohol of the formula 4 with methylamine to give the enantiomerically pure alcohol of the formula 1.

2. A process according to claim 1, wherein the reduction in step (i) is performed using $NaBH_4$.

3. A process according to claim 1, wherein the lipase in step (ii) is an immobilized lipase.

4. A process according to claim 1, wherein the lipase in step (ii) is derived from Burkholderia or Pseudomonas.

5. A process according to claim 1, wherein the separation in step (iii) takes place in the form of the conjugated base of the succinic semiester of the formula 7.

6. A process according to claim 1, wherein the reaction of step (ii) is carried out in a hydrocarbon as solvent.

7. A process according to claim 6, wherein heptane is used as the solvent.

8. A process according to claim 1, wherein the process is operated continuously.

9. A process according to claim 8, wherein an immobilized lipase is used in a column reactor.

10. A process according to claim 9, wherein ethylene carbonate or propylene carbonate is used as the solvent in step (ii).

11. A process according to claim 2, wherein the lipase in step (ii) is an immobilized lipase.

12. A process according to claim 11, wherein the separation in step (iii) takes place in the form of the conjugated base of the succinic semiester of the formula 7.

13. A process according to claim 12, wherein the reaction of step (ii) is carried out in a hydrocarbon as solvent.

14. A process according to claim 13, wherein heptane is used as the solvent.

15. A process according to claim 14, wherein the process is operated continuously.

16. A process according to claim 15, wherein an immobilized lipase is used in a column reactor.

17. A process according to claim 16, wherein ethylene carbonate or propylene carbonate is used as the solvent in step (ii).

* * * * *